(12) United States Patent
Horn (10) Patent No.: US 8,759,112 B2
(45) Date of Patent: Jun. 24, 2014

(54) MULTIFUNCTIONAL REFERENCE SYSTEM FOR ANALYTE DETERMINATIONS BY FLUORESCENCE

(75) Inventor: Carina Horn, Biblis (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 429 days.

(21) Appl. No.: 11/666,198

(22) PCT Filed: Oct. 25, 2005

(86) PCT No.: PCT/EP2005/011448
§ 371 (c)(1),
(2), (4) Date: Sep. 21, 2007

(87) PCT Pub. No.: WO2006/045596
PCT Pub. Date: May 4, 2006

(65) Prior Publication Data
US 2008/0014655 A1   Jan. 17, 2008

(30) Foreign Application Priority Data

Oct. 25, 2004 (DE) .......................... 10 2004 051 830

(51) Int. Cl.
*G01N 21/76* (2006.01)

(52) U.S. Cl.
USPC ................. 436/172; 252/301.16; 252/301.36; 252/700

(58) Field of Classification Search
None
See application file for complete search history.

(56) References Cited

U.S. PATENT DOCUMENTS

| 4,255,053 | A | | 3/1981 | Lubbers et al. |
| 4,420,566 | A | | 12/1983 | Jessop et al. |
| 5,057,427 | A | * | 10/1991 | Wald et al. ..................... 435/280 |
| 5,114,350 | A | | 5/1992 | Hewett |
| 5,151,603 | A | | 9/1992 | Nakamura |
| 5,194,393 | A | | 3/1993 | Hugl et al. |
| 5,591,400 | A | | 1/1997 | Dektar et al. |
| 5,672,515 | A | | 9/1997 | Furlong |
| 6,204,067 | B1 | | 3/2001 | Simon et al. |
| 6,602,716 | B1 | | 8/2003 | Klimant |
| 6,730,471 | B1 | | 5/2004 | Katerkamp et al. |
| 2003/0151741 | A1 | | 8/2003 | Wolleschensky et al. |
| 2004/0136871 | A1 | | 7/2004 | Pachl et al. |
| 2004/0171094 | A1 | | 9/2004 | Klimant et al. |

FOREIGN PATENT DOCUMENTS

| DE | 3852108 T2 | 3/1995 |
| DE | 69513683 T2 | 6/2000 |
| DE | 19903506 A1 | 8/2000 |

(Continued)

OTHER PUBLICATIONS

Fayed et al., "Dual emission of chalcone-analogue dyes emitting in the red region", Chemical Physics, vol. 303 pp. 317-326 (2004).*

(Continued)

*Primary Examiner* — Dirk Bass
(74) *Attorney, Agent, or Firm* — Roche Diagnostics Operations, Inc.

(57) ABSTRACT

The present invention concerns a system and method for the luminescence detection of an analyte in a liquid sample. The system comprises a support on which an analyte-specific substance and a reference substance are located. The analyte-specific substance is able to emit a first luminescence signal on contact with the analyte and the reference substance is able to emit a second luminescence signal which is substantially quenched by contact with the liquid sample.

13 Claims, 9 Drawing Sheets

(56) References Cited

FOREIGN PATENT DOCUMENTS

| | | | |
|---|---|---|---|
| DE | 69630531 | T2 | 8/2004 |
| EP | 1394219 | | 3/2004 |
| JP | 0317662 | A | 11/1990 |
| JP | 2002506973 | T | 5/2002 |
| JP | 2004138619 | A | 5/2004 |
| JP | 2005528896 | T | 9/2005 |
| JP | 2005532570 | T | 10/2005 |
| WO | 83/00931 | A1 | 3/1983 |
| WO | 92/12424 | A1 | 7/1992 |
| WO | 99/06821 | A1 | 2/1999 |
| WO | WO 02/056023 | | 7/2002 |
| WO | WO 02/103334 | A1 | 12/2002 |

OTHER PUBLICATIONS

Shamsipur et al., Analytica Chimica Acta 501(2004)55-60.

Lin et al., "Fluorescence lifetime characterization of novel low-pH probes", Analytical Biochemistry vol. 294, No. 2 118-125 (Jul. 15, 2001).

Dobretsov et al., "4-Dimethylaminochalcone and 3-Methoxybenzanthrone as Fluorescent Probes to Study Biomembranes II. Sensitivity of 4-Dimethylaminochalcone to Water Molecules in the Surface Layer of a Membrane", Studia Biophysica, Berlin, 71 (3), 181-187 (1978).

JP Office Action for Patent Application No. 537234/2007 mailed Sep. 14, 2010.

* cited by examiner

3) pH change as signal generator

MULTIFUNCTIONAL REFERENCE SYSTEM FOR ANALYTE DETERMINATIONS BY FLUORESCENCE

REFERENCE TO RELATED APPLICATIONS

This application claims priority to PCT/EP2005/011448 filed Oct. 25, 2005 and DE 10 2004 051 830.0 filed Oct. 25, 2004.

TECHNICAL FIELD

The invention concerns a system for the luminescence detection of an analyte in a liquid sample.

BACKGROUND

Luminescence detection and in particular fluorescence detection systems have been known for a long time in the prior art. In current analytical methods the photometric evaluation of analytical test elements is one of the most common methods for rapidly detecting or rapidly determining the concentration of analytes in samples. In general photometric evaluations are used in the field of analytics, environmental analytics and above all in the field of medical diagnostics. Test elements which are evaluated photometrically are very important especially in the field of blood glucose diagnosis from capillary blood.

In fluorescence-spectrometric detection systems, the intensity of the emission of the fluorescent substances is directly proportional to the intensity of the excitation. The intensity of excitation can be influenced by many factors for example by the behaviour of the light source over time or changes in the light paths. Changes in the light path can give rise to different excitation intensities especially in a small instrument which is not fixed in a laboratory for measurement. Hence it is very difficult to reproducibly carry out absolute fluorescence measurements.

For this reason current fluorescence test systems use a reference substance to which the test can be referred. Various types of reference substances are known.

For example it is known in the prior art that a second fluorophore which emits at a different wavelength to that of the specific fluorophore for the analyte can be used in detection systems which are based on a fluorophore. Hence this second fluorophore can be used as a reference. The two fluorophores can be distinguished by using two different filters (and two detectors) wherein one fluorophore is not chemically converted and can be used as a reference. This detection system is for example described in the following literature reference: *Principles of Fluorescence Spectroscopy*, J. R. Lackowicz, Kluver Academic/Plenum Publishers, New York, Boston, Dordrecht, Moscow 1999, 2$^{nd}$ edition.

Another approach is a time-resolved and phase-modulated referencing in which a very long-lived fluorophore which has a longer lifetime than a short-lived fluorophore that is specific for the analyte, is used as a reference substance. Whereas the parameters of the long-lived luminescence are not influenced by the analyte, the intensity of the short-lived luminophore which is specific for the analyte changes depending on the respective analyte concentration. Then time-resolved measurement allows firstly the analyte fluorophore to be measured and subsequently the decay of the reference is recorded. The ratio of the decay signal to the signal of the analyte plus that of the reference substance must always be the same independent of the intensity of the irradiation.

WO 99/06821, also published as U.S. Pat. No. 6,602,716 (B1), discloses such a system. In this case at least two different luminescent materials are used which are co-immobilized on a support, the first of which responds to the parameter of the analyte to be determined at least as regards luminescence intensity and the second of which does not respond to the parameter to be measured at least as regards luminescence intensity and decay time. The luminescent materials have different decay times. The time or phase behaviour of the resulting luminescence response can thus be used to generate a reference variable for determining the parameter of the analyte to be measured.

WO 02/056023 discloses an optical sensor for determining at least one parameter in a sample in which also in this case an indicator material which responds to the parameter with a short decay time and a reference material with a long decay time which does not respond to the parameter are used. The indicator material and the reference material are immobilized on a common support and are covered on the sample side with a light-impermeable layer.

However, referencing by means of a second fluorophore which is measured at a different wavelength requires a much more elaborate apparatus. Thus for example two filters are required instead of only a single filter in order to block the excitation light and usually two detectors are also necessary. Furthermore, due to the fact that the optical paths are separated after the excitation into different detectors, one of the two paths may be defective which would then result in an incorrect referencing.

A disadvantage of time-resolved or phase-resolved referencing is that the measurements of the analyte always have to be carried out against a luminescent background. This means that there is always a certain offset or signal background which limits the measuring range. This principle is shown for example in FIG. 1.

Figure 1:
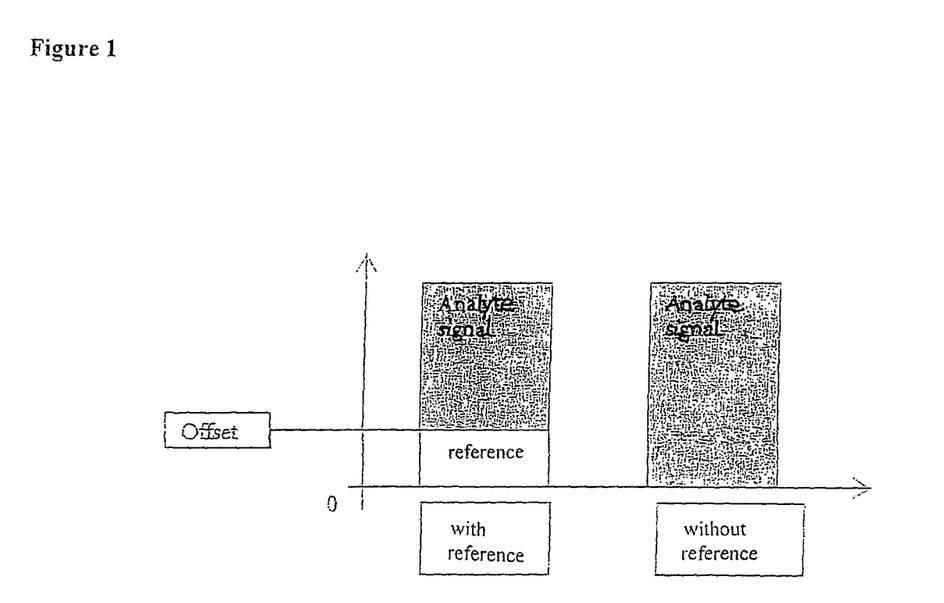
FIG. 1 shows the measuring range for the measurement of the luminescence signal of an analyte with and without a reference substance according to methods of the prior art.

FIG. 1 shows the measuring range of the analyte signal with and without the reference. Without the reference fluorophore it is possible to optimally adapt the measuring range to the dynamic range that has to be spanned. With the reference fluorophore a part of the measuring range is used by the reference.

The reference substances or reference luminescent substances which are used in the above-mentioned methods of the prior art can only be used as a reference substance for comparison with the analyte but they cannot fulfil further functions.

However, an important issue when determining analytes in the diagnostic field is also detection of wetting and/or a filling control of the test field.

There are additional approaches in this field, such as, WO 83/00931, also published as U.S. Pat. No. 4,420,566, which discloses a device and a method for detecting a liquid sample in which it is determined whether an adequate amount of sample liquid has been applied. This is achieved by a drop detector which comprises a light source that projects radiation onto the sample, said radiation being within the absorption band of water. The sample carrier is firstly irradiated in a dry state and then in the wetted state and thus the moisture is measured. The moisture content of the sample is then calculated from the difference between the detected signals.

U.S. Pat. No. 5,114,350 discloses a method and a device for determining the concentration of an analyte in a sample of body fluid. The degree of wetting of the reaction support is measured by measuring the amount of reflected light which decreases with increasing wetting.

DE 10248555 A1, also published as US 2004/136,871, discloses a method for detecting and compensating for an under-dosing of test strips. A test element is described in this document which comprises an analyte-specific reagent which interacts with an analyte in a sample, and a control substance which interacts with a sample matrix of the sample. The analyte-specific reagent interacts with the analyte depending on the analyte concentration in a detection wavelength range. When the test field is irradiated, the control sequence interacts with the sample matrix as a function of the amount of sample applied to the test field. The control substance can also react with the water contained in the sample matrix. One example which is mentioned in DE 10248555 A1, also published as US 2004/136,871, uses chlorophenol red as an analyte-independent colour former for determining the amount of sample and 2,18-phosphomolybdic acid as an analyte-specific reagent for determining the glucose concentration in a sample e.g. a blood sample. Thus in the said example of this document two wavelength ranges have to be detected which complicates the apparatus for this test system.

SUMMARY

A system and method for detecting an analyte in a liquid sample is provided which can be carried out with a reference substance and an analyte-specific substance without necessitating the elaborate apparatus described in the prior art.

A system for the luminescence detection of an analyte in a liquid sample is provided comprising a support including an analyte-specific substance which is able to emit a first luminescence signal on contact with the analyte and a reference substance which is able to emit a second luminescence signal which is substantially quenched by contact with the liquid sample.

The known detection methods from the prior art can be simplified according to the invention by using a reference substance which emits a luminescence signal in the absence of the sample that can be used as a reference signal. When the sample is added, this luminescence signal is abruptly and substantially quenched i.e. it generates essentially no more signal or at least a very greatly reduced signal.

In an embodiment of the present invention excitation and emission are at approximately the same wavelengths as for the analyte-specific substance. This means that a single detector can be then used to detect the luminescence signals.

Other features and embodiments of the present invention will become apparent from the following detailed description. It should be understood, however, that the detailed description and the specific examples, while indicating embodiments of the invention, are given by way of illustration only, since various changes and modifications within the spirit and scope of the invention will become apparent to those skilled in the art from this detailed description.

BRIEF DESCRIPTION OF THE DRAWINGS

Below, the invention is explained in detail based on the embodiments represented schematically in the drawings. The following are shown respectively in the longitudinal cross section:

FIG. 9 shows a test system using LysoSensor Blue DND-167, NA) and a buffer pH=5. Four solutions containing 0 mg/dl, 90 mg/dl, 300 mg/dl and 700 mg/dl glucose and a buffer of pH=7 were used as samples. The intensity of the luminescence was measured for 24 seconds after applying the sample. The sample solution pH=7 resulted in a rebuffering of the layer which contained LysoSensor Blue DND-167. The results with the sample which contained 0 mg/dl glucose correspond with the result from FIG. 8. As the glucose concentration increases, the decrease in the time-dependent luminescence becomes smaller (90 mg/dl) or the luminescence increases above the initial value (300 mg/dl and 700 mg/dl glucose). The different time courses of the LysoSensor Blue DND-167-dependent luminescence and NADH-dependent luminescent can be clearly distinguished from one another.

DETAILED DESCRIPTION OF THE DRAWINGS

The property of the reference substance to emit a luminescence signal in the absence of the sample which is then quenched on contact with the sample allows the reference substance to not only be used to detect the analyte but also to determine the amount of sample, to determine the amount of analyte and/or the operational readiness of the support. The reference substance can for example be selected such that its luminescence signal is quenched when it is wetted. Then the operational readiness of the test system can be made visible. If the support which comprises the test system has for example become wet during storage or such like or if other substances have come into contact with the support, this luminescence signal of the reference substance will be quenched and it is discernible that this test system is not ready to operate.

In an embodiment of the invention, the quenching is reversible i.e. if the sample or in particular the wetting is removed or reversed, the luminescence signal can also be re-established.

Thus in addition to referencing, this also allows a wetting detection and/or filling control to be achieved with the system according to the invention. If, for example, a test field is provided on the support and it is not completely wetted by the sample, a residual luminescence signal remains. It is then possible to make a calculated correction with regard to the analyte signal by means of this residual luminescence.

If the luminescence properties with regard to the ambient humidity are reversible, such a reference substance can also be used as a humidity indicator. The humidity indicator then gives information about the storage conditions of the test system and its operational readiness. Hence, the reference substance can also be used as an indicator for a selected expiry date of the test system.

Luminescence substances and in particular fluorophores which have such properties are hardly known in the prior art. Most fluorophores do not increase their fluorescence and are not quenched in a moist environment.

If the luminescence properties of the analyte-specific substance depend on the pH, the analyte-specific substance can be used to determine the pH. Hence in one embodiment the system according to the invention is a pH sensor i.e. a system in which the analyte-specific substance is selected from substances whose luminescence signal depends on the pH. In an embodiment the reference substance is not a substance whose luminescence signal is significantly quenched by a change in pH. An example of an analyte-specific substance is LysoSensor Blue DND-167 or a derivative thereof e.g. for determining the pH in the range of about 3.5 to about 7.0 or about 4.5 to about 6.0.

Before the sample is applied, the support of the pH sensor, for example, has a pH at which the analyte-specific substance exhibits essentially no luminescence. In the case of LysoSensor Blue DND-167 this can be a pH selected from the range of about 7 to about 10 or from about 8 to about 9.

Moreover, the buffering power of the support can be predetermined in such a manner that the support is essentially completely rebuffered to the pH of the sample. A person skilled in the art knows how such a buffering power of the support has to be adjusted.

In principle all substances come into consideration as the reference substance which is able to emit a luminescence signal which is substantially quenched by contact with the sample. All types of substances can be used for this whose luminescence signal is quenched by contact with some component of the sample. Components in samples to be examined which trigger quenching can for example be water, calcium, magnesium or other metals or ions thereof, the pH as well as other factors.

In an embodiment, if water is the factor that triggers quenching, the reference substance is selected from the class of chalcones of formula I.

Chalcones are known in the prior art (B. M. Krasovitskii, D. G. Pereyaslova, Z H. Vsesoyuznogo Obscchestva in D. I. Mendeleeva, 10 (6), 704 (1965); G. E. Dobretsov, V. A. Petrov, Yu. A. Vladimirov, "Studia Biophysica" Berlin, 71 (3), 181-187 (1978)).

In an embodiment, substances are of the general formula I.

in which one of the residues $R_2$, $R_3$ and $R_5$ is selected from $NR_{11}R_{12}$ and $SO_3Na$. The other substituents $R_1$, $R_4$, $R_6$, $R_7$, $R_8$, $R_9$ and $R_{10}$ can be any substituents and in an embodiment include hydrogen or halogen. Examples of suitable halogens include F, Cl, Br and I.

$R_{11}$ and $R_{12}$ are selected from hydrogen, $C_1$-$C_4$ alkyl, in particular methyl, ethyl, propyl and butyl, in which $C_1$-$C_4$ alkyl can be substituted with —OH, —SH, phosphate, —COOH, —NH$_2$, —SO$_3$Na, —NO$_2$, halogen and in particular F, Cl, Br and I. An example of a substituted alkyl residue is $CH_2CH_2$—$SO_3Na$.

Additional examples of substances which are suitable as a reference substance according to the invention are aminochalcones and chlorochalcones. A specific example of suitable reference substances are of the general formulae II, III und IV.

Chlorochalcone was prepared according to the method of Krasovitskii (B. M. Krasovitskii, D. G. Pereyaslova, Z H. Vsesoyuznogo Obscchestva in D. I. Mendeleeva, 10 (6), 704 (1965)).

Aminochalcone in which $R_{11}$ and $R_{12}$ are methyl, is commercially available and was used for preliminary investigations.

The aminochalcone of the general formula V, in which $R_{11}$ and $R_{12}$ are both $CH_2CH_2$—$SO_3Na$ was prepared by a multistep synthesis.

Hence another substance is that of formula V.

The quench reaction can also be caused by metal ions. Thus compounds whose luminescence signal is substantially quenched on contact with metal ions are also suitable according to the invention as reference substances.

It is possible to select reference substances in which the luminescence signal is quenched by contact with calcium or magnesium ions. Fluorescent dyes which stop fluorescing or fluoresce to a greatly reduced extent when they form a complex with $Ca^{2+}$ and/or $Mg^{2+}$ are for example suitable for this purpose.

An example of such a fluorescent dye is FuraRED which is obtainable from the Molprobes company. FuraRED has the following structure:

A third reference substance that is suitable according to the invention is one which responds to a change in pH. These are substances whose luminescence signal is substantially quenched when the pH changes.

This is particularly advantageous for samples such as blood. Blood has a very high buffering power and is therefore able to alter a previously set pH in the test system. If the test system is for example set to a low pH (for example pH 5), the test system is rebuffered to pH 7 when a blood sample is applied.

An example of such a reference substance is LysoSensor Blue DND-167 from Molprobes (catalogue No. L7533, ABS/EM' (nm): 373/425, PKA: 5.1, suitable pH-range: 4.5-6.0). LysoSensor Blue DND-167

Derivatives of LysoSensor Blue DND-167 which have a better water solubility than LysoSensor Blue DND-167 can additionally be used for the system according to the invention or for the method according to the invention. The increased water solubility can increase the reaction rate with the sample containing the analyte.

In the inventive derivatives of LysoSensor Blue DND-167 one or more hydrogen atoms are independently of one another replaced by substituents in which case one carbon atom can carry more than one substituent. Polar substituents which can carry at least one positive or/and negative charge are particularly suitable substituents.

All positions of the anthracene backbone occupied by hydrogen, the two morpholinyl groups and the two methylene groups of LysoSensor Blue DND-167 are suitable for a substitution according to the invention.

In an embodiment, the derivatives according to the invention of LysoSensor Blue DND-167 carry exactly one, two, three or four substituents.

Examples of suitable substituents include —OH, —SH, phosphate, —$COOR_{11}$, —$NR_{11}R_{12}$, —$SO_3Na$, —$NO_2$, halogen, in particular F, Cl, Br and I. $R_{11}$ and $R_{12}$ are selected from hydrogen, $C_1$-$C_4$ alkyl, in particular methyl, ethyl, propyl and butyl, where $C_1$-$C_4$ alkyl can be substituted with —OH, —SH, phosphate, —COOH, —$NH_2$, —$SO_3Na$, —$NO_2$, halogen, in particular F, Cl, Br and I. An example of a suitable substituted alkyl residue is $CH_2CH_2$—$SO_3Na$.

An example of a derivative of LysoSensor Blue DND-167 is a compound of formula VII:

In an embodiment the system according to the invention is a system for determining glucose and in particular blood glucose. NAD or NADP can for example be used as the analyte-specific substance which, in the presence of a suitable enzyme e.g. a glucose dehydrogenase, forms NADH or NADPH which exhibits luminescence. A substance whose luminescence signal is substantially quenched when the pH changes e.g. LysoSensor Blue DND-167 or a derivative thereof is for example used as a reference substance in the system according to the invention for the determination of glucose.

Another subject matter of the present invention is also a method for detecting an analyte in a liquid sample by luminescence comprising: Providing a support comprising an analyte-specific substance which is able to emit a first luminescence signal on contact with the analyte, and comprising a reference substance which is able to emit a second luminescence signal which is substantially quenched by contact with the liquid sample, contacting the support with a liquid sample which contains an analyte to be detected and measuring the luminescence signals and detecting the analyte by comparing the luminescence signals.

As already mentioned above, it is also suitable in this method to use a reference substance and an analyte-specific substance which are excited and emit in essentially the same wavelength range. For example, the luminescence signal of the reference substance is firstly measured in the absence of sample, subsequently the liquid sample is applied and the luminescence signal is measured which is caused by the sample. This can be carried out by using a single detector. It is, however, also possible to use different detectors especially when the wavelength ranges of the reference substance and the analyte-specific substance differ.

EXAMPLES

Example 1

The function of dimethylaminochalcone was examined in a simple formulation. Since this chalcone is not water-soluble, methanol was used as a water substitute.

In this case it was already visually discernible that the chalcone which strongly fluoresced under UV light in a dry state abruptly exhibited no more fluorescence when a drop of MeOH is applied.

Test Formulation I:

| | |
|---|---|
| dimethylaminochalcone | 0.2 g |
| MeOH | 25 ml |
| Transpafill | 5 g |
| Propiofan | 0.5 g |

The chalcone was dissolved in MeOH and Transpafill was added. Propiofan was added to this mixture and the slurry was homogenized. Subsequently the mixture was knife-coated onto a Pokalon foil and dried for 5 minutes at 50° C.

Figure 2:
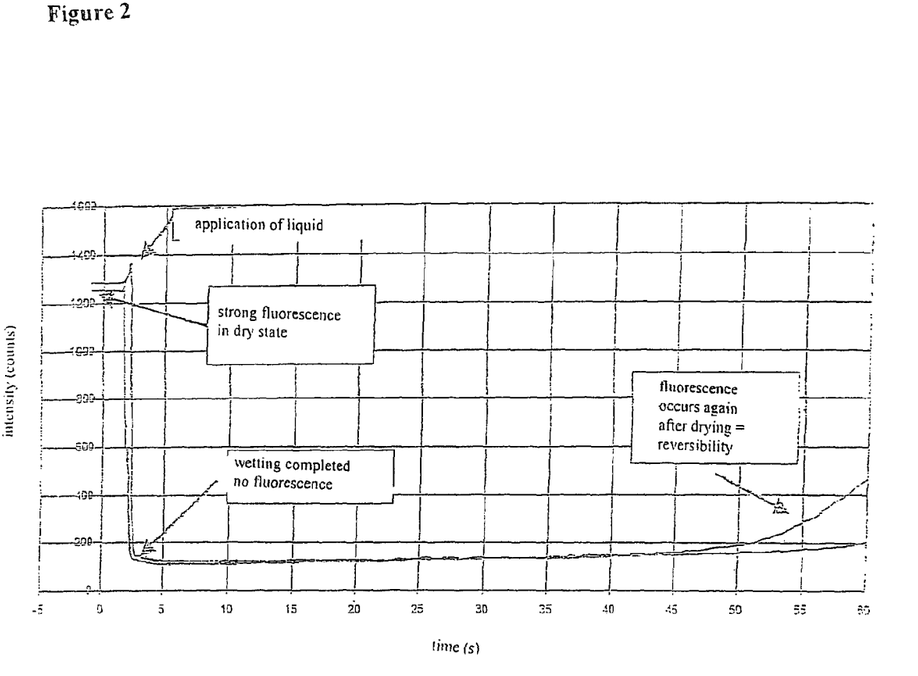
FIG. 2 shows the kinetics of the quenching of dimethylaminochalcone when wetted.
Figure 3:
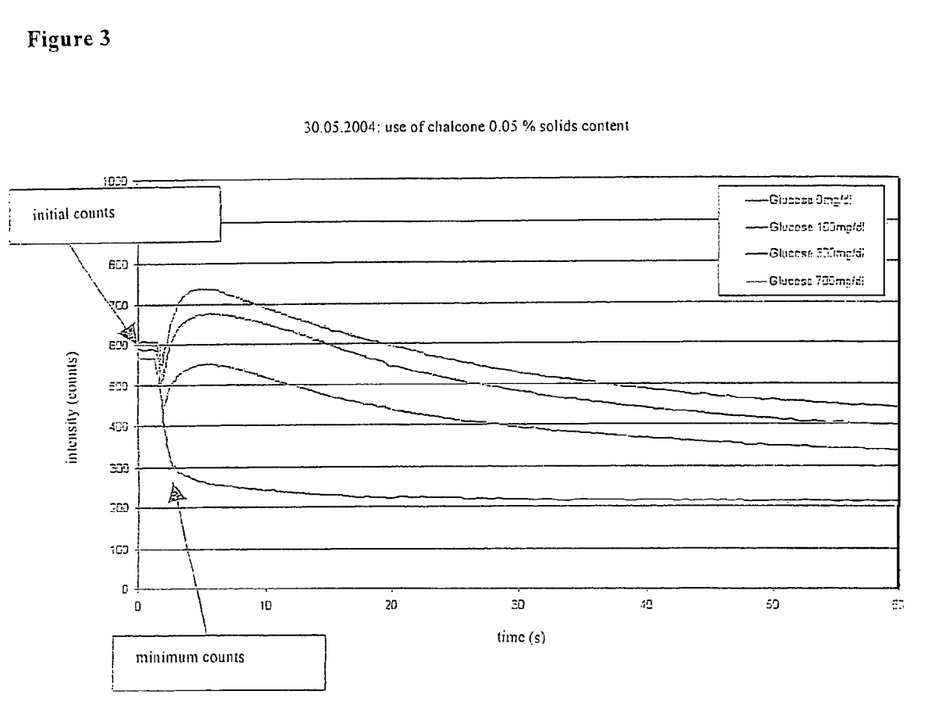
FIG. 3 shows a test system using a chalcone containing 0.05% solids. 4 Solutions each containing 0 mg/dl, 100 mg/dl, 300 mg/dl and 700 mg/dl glucose were used as samples. The intensity of the luminescence was measured and compared with the quenched signal which was derived from the control sample containing 0 mg/dl glucose. The difference counts are at a maximum when sufficient sample was applied. They become smaller and smaller the less sample is applied.
Figure 4:
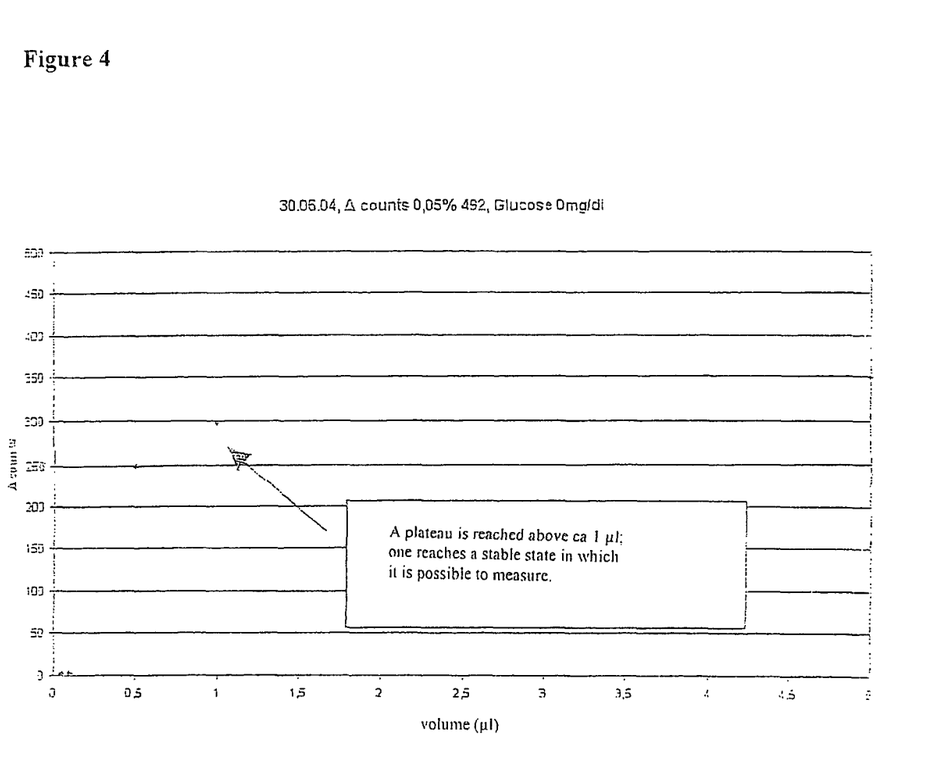
FIG. 4 shows the number of counts per volume in the same test format as described in FIG. 3. A plateau is reached above about 1 µl, below which no reliable measurement is possible.
Figure 5:
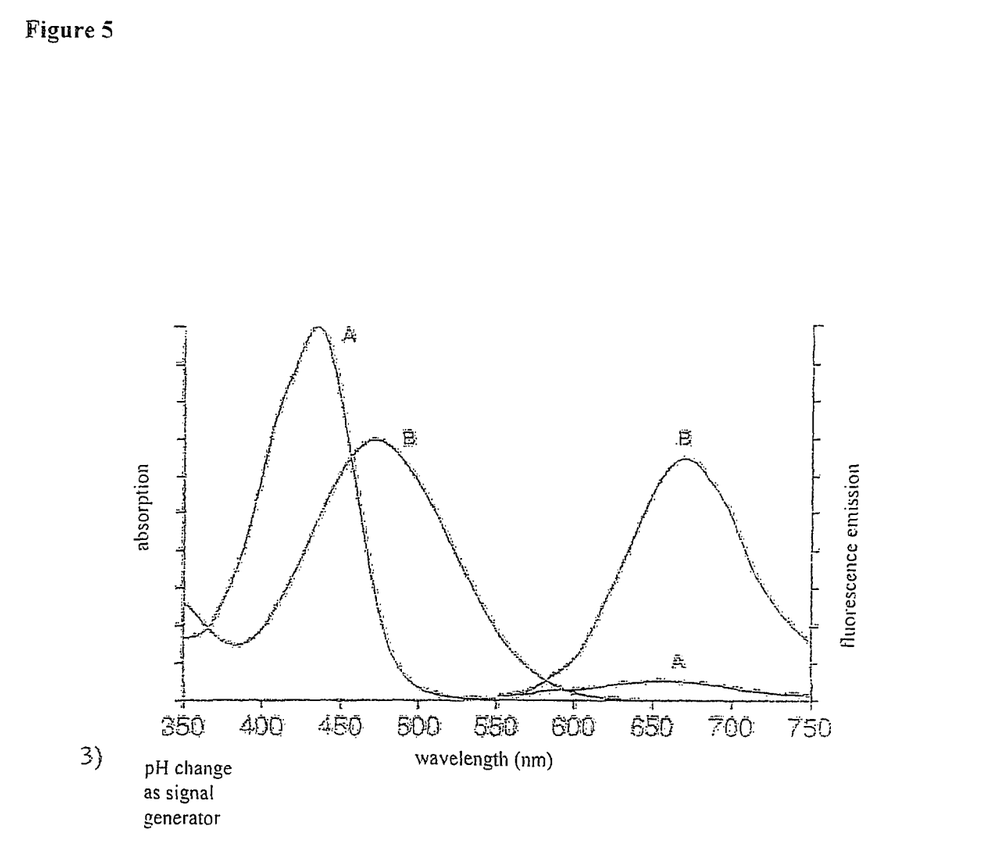
FIG. 5 shows the absorption and emission spectrum of FuraRED (Molucular Probes, Eugene, Oreg.).
Figure 6:
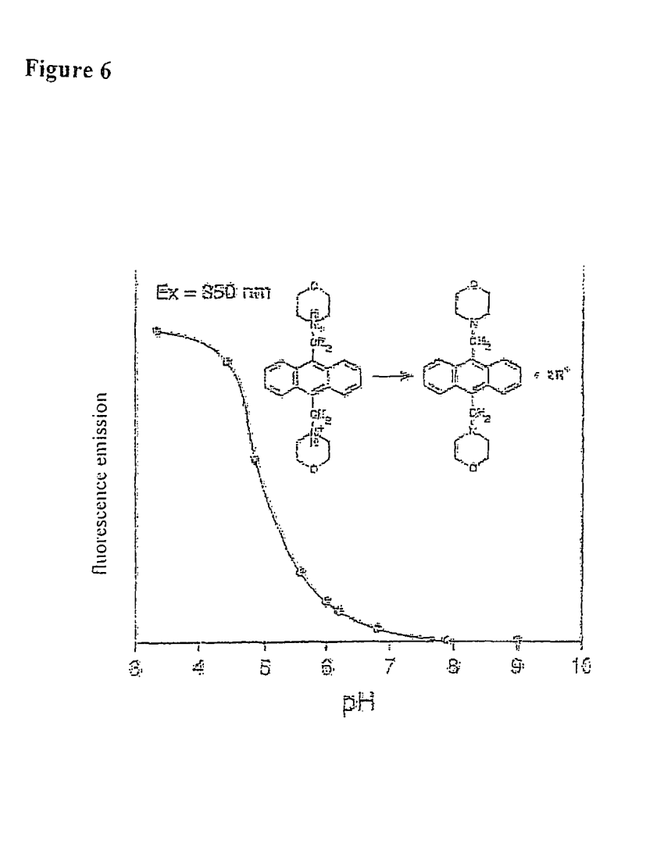
FIG. 6 and FIG. 7 show the fluorescence emission of LysoSensor Blue DND-167 (Molecular Probes, Eugene, Oreg.) versus the pH.

The measurement shown in FIG. 2 shows the kinetics of the quenching when one drop of methanol is applied to the greenish luminescent layer which was knife-coated onto the Pokalon foil. It can be quite clearly seen that the application of methanol results in an abrupt quenching which is, however, reversible as soon as the methanol evaporates i.e. dries again from the chalcone layer.

Example 2

1 Dependency of the Fluorescence on the pH

The dye LysoSensor Blue DND-167 was dissolved in various buffers having different pH values and these solutions were applied to a test strip which only contained a blank foil as drop-on surface. These were measured on the measuring instrument.

Excitation wavelength: 375 nm (UV-LED from the Roithner Company), detection at 420 nm with the aid of a fluorescence filter, Langpass, KV 418 from the Schott Company, detector BPW34.

Figure 7:
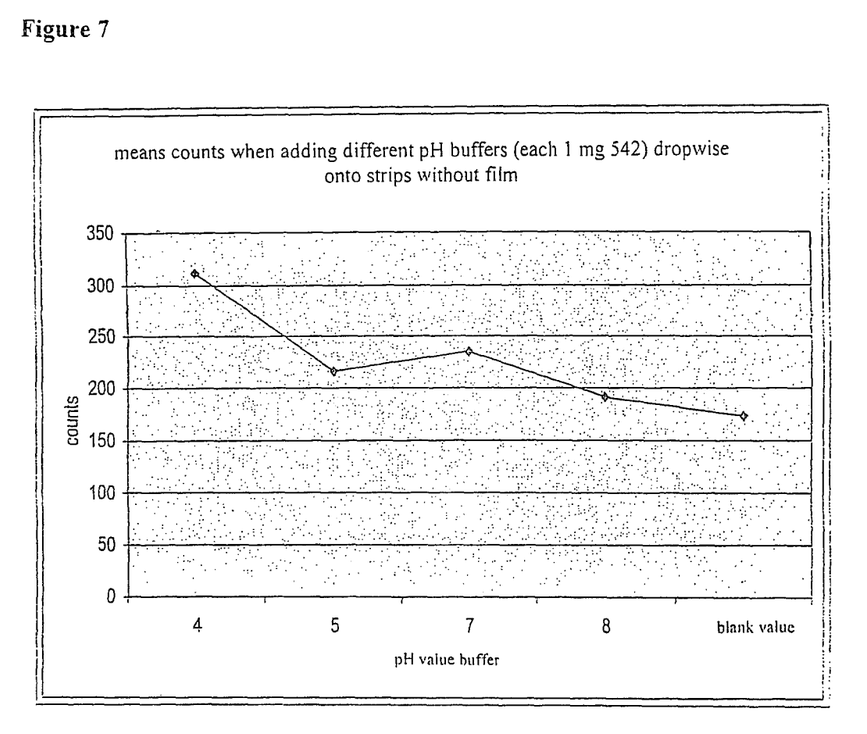

The results are compiled in FIG. 7 (blank value=solution without dye). The fluorescence decreases as the pH increases. At pH=8 the blank value is almost reached.

2 Dye LysoSensor Blue DND-167 in a Layer at pH 5

A layer was prepared which contained glucose dehydrogenase, NAD and a buffer. The pH of the layer was 5.

Figure 8:
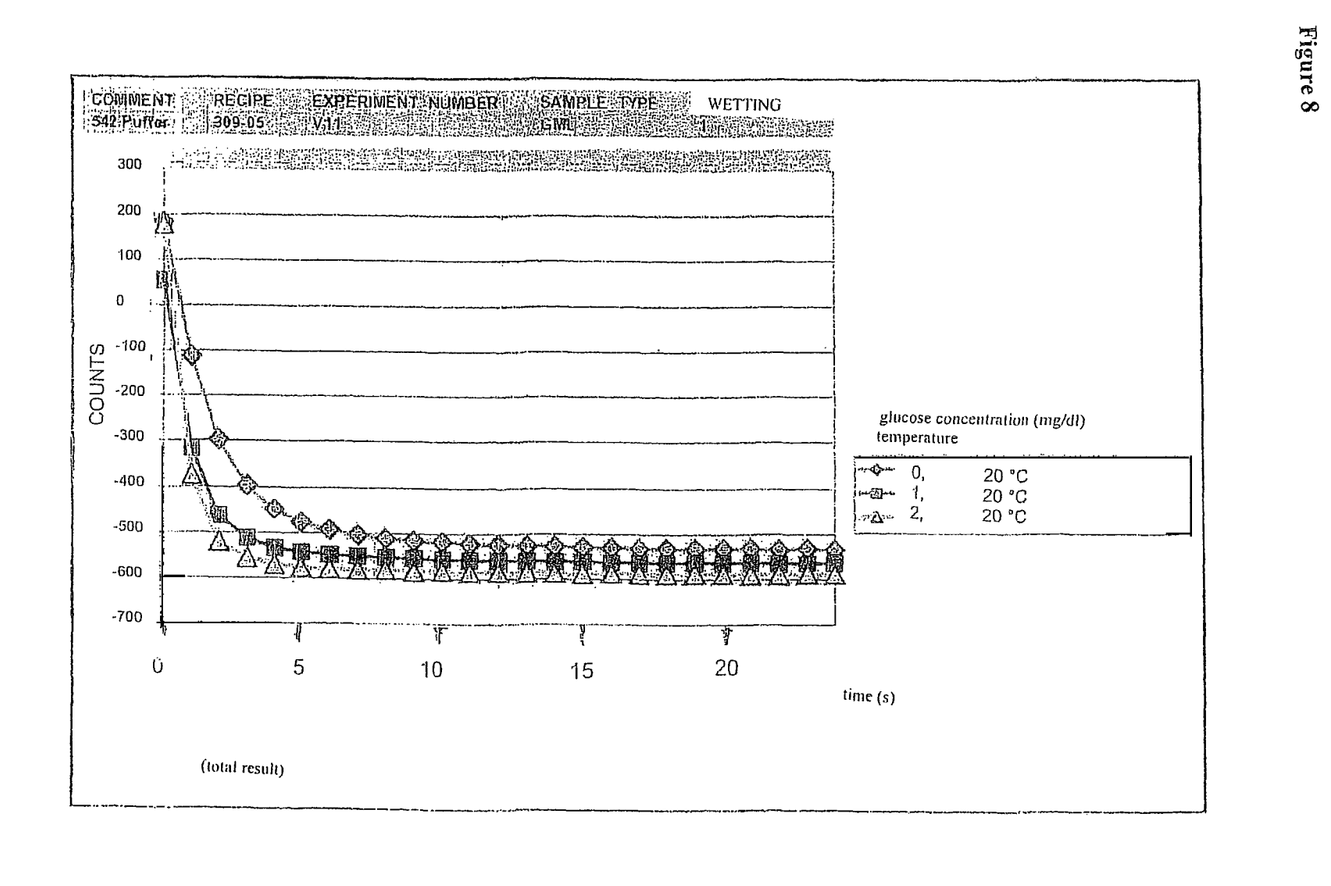
FIG. 8 shows a test system using LysoSensor Blue DND-167, NAD and a buffer pH=5. Three solutions containing 0 mg/dl, 1 mg/dl and 2 mg/dl glucose and a buffer pH=7 were used as samples. The intensity of the luminescence was measured for 24 seconds after applying the sample. The sample solution pH=7 resulted in a rebuffering of the layer which contained LysoSensor Blue DND-167. A time-dependent decrease of the luminescence was observed. Virtually no further change in the luminescence was measured after 24 seconds.

FIG. 8 shows the decrease of fluorescence when the buffer solution pH 7 was added dropwise. In this process the pH of the layer was rebuffered from pH 5 to pH 7. The fluorescence decreased during the rebuffering.

Figure 9:
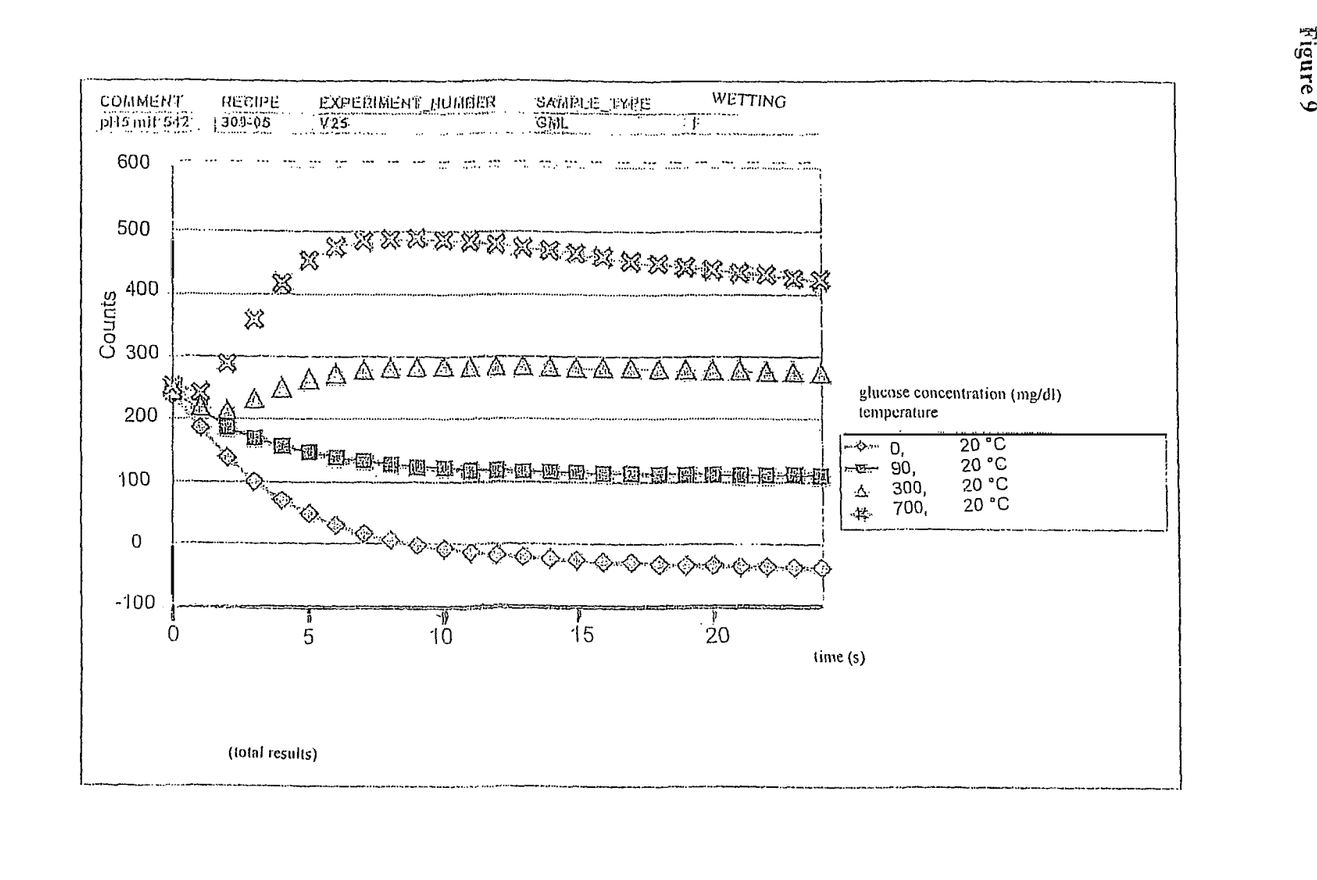

In another experiment buffered glucose solution was added dropwise to the layer. A superimposed reaction was discernible; on the one hand, the fluorescence decreased due to the rebuffering of the dye (cf. FIG. 8), on the other hand, fluorescent NADH was formed by the glucose reaction which corresponds to the glucose concentration. The results are shown in FIG. 9.

Having described the invention in detail and by reference to specific embodiments thereof, it will be apparent that modification and variations are possible without departing from the scope of the invention defined in the appended claims. More specifically, although some aspects of the present invention are identified herein, it is contemplated that the present invention is not necessarily limed to these aspects of the invention.

What is claimed is:

1. System for the luminescence detection of an analyte in a liquid sample comprising:
   (a) a support including an analyte-specific substance which is able to emit a first luminescence signal on contact with the analyte, a reference substance which is able to emit a second luminescence signal which is substantially quenched by contact with the liquid sample, wherein the analyte-specific substance and the reference substance are excitable at essentially the same wavelengths and emit at essentially the same wavelengths, and wherein the analyte-specific substance and the reference substance are fluorophores, and the reference substance is wherein one of $R_2$, $R_3$ and $R_5$ is selected from the group consisting of $NR_{11}R_{12}$ and $SO_3Na$;
$R_{11}$ and $R_{12}$ are selected from the group consisting of hydrogen and $C_1$-$C_4$ alkyl; and
$R_1$, $R_4$, $R_6$, $R_7$, $R_8$, $R_9$ and $R_{10}$ are selected from the group consisting of hydrogen and a halogen; and
   (b) a single detector which is adapted to measure the luminescence signals of the analyte-specific substance and of the reference substance.

2. System of claim 1, further comprising an evaluation unit formed to determine the amount of sample, the amount of analyte and operational readiness of the support.

3. System of claim 1, wherein the reference substance has a luminescence signal that is substantially quenched on contact with water.

4. System of claim 1, wherein the analyte-specific substance is selected from substances whose luminescence signal depends on the pH.

5. System of claim 4, wherein the analyte-specific substance is

6. System of claim 4, wherein the analyte-specific substance is

7. System of claim 1, wherein the reference substance is selected from the group consisting essentially of aminochalcones and chlorochalcones.

8. System of claim 1, wherein the reference substance is

9. System of claim 1, wherein the reference substance is

10. System of claim 1, wherein the reference substance is

11. Method for detecting an analyte in a liquid sample by luminescence comprising:
   i) providing a support including an analyte-specific substance which is able to emit a first luminescence signal on contact with the analyte, a reference substance which is able to emit a second luminescence signal which is substantially quenched by contact with the liquid sample, wherein the analyte-specific substance and the reference substance are excitable at essentially the same wavelengths and emit at essentially the same wavelengths, and wherein the analyte-specific substance and the reference substance are fluorophores, and the reference substance is wherein one of $R_2$, $R_3$ and $R_5$ is selected from the group consisting of $NR_{11}R_{12}$ and $SO_3Na$;
   $R_{11}$ and $R_{12}$ are selected from the group consisting of hydrogen and $C_1$-$C_4$ alkyl; and
   $R_1$, $R_4$, $R_6$, $R_7$, $R_8$, $R_9$ and $R_{10}$ are selected from the group consisting of hydrogen and a halogen,
   ii) contacting the support with a liquid sample which contains an analyte to be detected and
   iii) measuring the luminescence signals and detecting the analyte by comparing the luminescence signals.

12. Method of claim 11, wherein the luminescence signal of the reference substance is measured before bringing the support into contact with the liquid sample.

13. The method of claim 11 further comprising the step of providing an evaluation unit formed to determine the amount of sample.

* * * * *